(12) United States Patent
Ezenwa

(10) Patent No.: US 7,670,386 B2
(45) Date of Patent: Mar. 2, 2010

(54) PROSTHETIC SOCKET WITH REAL-TIME DYNAMIC CONTROL OF PRESSURE POINTS

(75) Inventor: Bertram Ezenwa, Mequon, WI (US)

(73) Assignee: WiSys Technology Foundation, Madison, WI (US)

( * ) Notice: Subject to any disclaimer, the term of this patent is extended or adjusted under 35 U.S.C. 154(b) by 78 days.

(21) Appl. No.: 11/958,940

(22) Filed: Dec. 18, 2007

(65) Prior Publication Data

US 2008/0147204 A1 Jun. 19, 2008

Related U.S. Application Data

(60) Provisional application No. 60/870,492, filed on Dec. 18, 2006.

(51) Int. Cl.
*A61F 2/80* (2006.01)
(52) U.S. Cl. ....................................................... 623/37
(58) Field of Classification Search .............. 623/32–37
See application file for complete search history.

(56) References Cited

U.S. PATENT DOCUMENTS

| 3,548,420 A | 12/1970 | Spence |
|---|---|---|
| 4,521,685 A | 6/1985 | Rebman |
| 4,745,812 A | 5/1988 | Amazeen |
| 6,544,292 B1 | 4/2003 | Laghi |
| 6,585,774 B2 | 7/2003 | Dean, Jr. et al. |
| 2003/0181990 A1 | 9/2003 | Phillips |
| 2004/0030411 A1 | 2/2004 | Caspers |

FOREIGN PATENT DOCUMENTS

| EP | 0870485 | 10/1998 |
|---|---|---|
| WO | WO 02/067825 | 9/2002 |
| WO | WO 02/085264 | 10/2002 |
| WO | WO 2004071337 | 8/2004 |

OTHER PUBLICATIONS

Kuhne, H., European Search Report, European Patent Office, Mar. 16, 2009, Berlin, Germany.

*Primary Examiner*—Bruce E Snow
(74) *Attorney, Agent, or Firm*—Boyle Fredrickson, S.C.

(57) ABSTRACT

An improved socket for a prosthesis uses a liner material providing fluid flow through a porous matrix whose local pressure is adjusted by a control system communicating with multiple valves and pressure sensors. Control of pressure in a viscoelastic material provides an improved trade-off between comfort and stability.

10 Claims, 3 Drawing Sheets

PROSTHETIC SOCKET WITH REAL-TIME DYNAMIC CONTROL OF PRESSURE POINTS

CROSS REFERENCE TO RELATED APPLICATION

This application claims the benefit of U.S. provisional application 60/870,492 filed Dec. 18, 2006 hereby incorporated by reference.

BACKGROUND OF THE INVENTION

The present invention relates to prosthetic devices, and in particular to a prosthetic device that may sense points of high pressure contact with a patient's residual limb and locally reduce those pressures on a dynamic basis.

Lower limb amputees may be fitted with a prosthetic leg that attaches to their residual limb by means of a socket surrounding the residual limb. In such cases, it is important that the socket fit closely to the residual limb so that the amputee has a sense that the prosthetic limb is secure and stable and the forces of walking are distributed evenly over the entire residual limb. It is also important that the fit not be so tight as to restrict blood flow or to be uncomfortable.

Unfortunately the volume of the residual limb changes significantly over time and even within the course of a day making a good fit between the residual limb and socket difficult to maintain. This change in the volume of the residual limb can be managed to some extent by the use of one or more socks which may be placed over the residual limb or removed from the residual limb at different times to adjust the fit of the socket.

Volume changes in the residual limb may also be accommodated by means of a socket incorporating one or more bladders that may be inflated manually by the patient, or automatically, to provide a desired pressure between the socket and the residual limb. For example, U.S. Pat. No. 6,585,774 describes a socket in a "pumping bladder" between the socket and the residual limb that makes use of forces developed during walking to pump additional fluids into other bladders within the socket to maintain a desired predetermined pressure between the socket and the residual limb. In this way, a good fit between the socket and the residual limb may be obtained despite variations in the volume of the residual limb.

A difficult problem for patients, even with padded sockets that properly conform to the surface of the residual limb, is the persistence of localized points of high pressure in the contact between the residual limb. Such persistent high pressure points can result from difficult to correct socket interface pressure that occurs during human activities such as running, jumping, leaning and lifting which cause large variations in the loading on the residual limb, and the need to maintain a relatively stiff interface between the residual limb and the socket to prevent undue "bouncing" movement of the prosthetic leg during use. Such persistent high pressure points may cause discomfort to the patient which can deter the use of the prosthetic leg and, in extreme cases, can cause tissue damage.

SUMMARY OF THE INVENTION

The present invention provides a cushioned socket for a prosthetic leg using a dynamically controlled system of pressure sensors and valves that selectively control the local pressure in a fluid filled and fluid permeable liner. The liner provides viscoelastic properties that moderate the pressure equalization process to reduce high pressure points while still providing a secure fit between the residual limb and the socket and facilitating multiple points of pressure control.

Specifically, the present invention provides a socket for the attachment of a prosthesis to a residual limb, the socket providing a compliant fluid charged material creating an interface between a rigid shell attached to the prosthesis and the residual limb. A plurality of sensors sense local pressure in the compliant fluid charged material and a set of actuators provide local control of the pressure between the compliant material and the residual limb. A control system communicates with the sensors and the actuators to anticipate points of high pressure between the residual limb and the compliant material to adjust the local pressure to reduce points of high pressure.

It is thus one object of one embodiment of the invention to provide for multiple zones of control pressure that anticipate the creation of high pressure points during use of the prosthesis.

The compliant fluid charged material may provide a substantially incompressible fluid with a predetermined viscosity moving through at least one porous matrix to provide viscous flow of the fluid under pressure.

It is thus another object of one embodiment of the invention to provide a material permitting the blending of multiple points of pressure control through viscoelastic flow.

The compliant fluid charged material may consist of at least two layers allowing fluid flow therebetween.

It is thus another object of one embodiment of the invention to provide for multiple dimensions of fluid flow permitting greater flexibility in the tailoring of the property at a given zone.

The porous matrix may be an elastomeric foam.

It is thus another object of one embodiment of the invention to provide a material that can have a controlled porosity allowing a variety of different materials to be readily implemented.

The porous matrix may be a gel material.

It is thus another object of one embodiment of the invention to make use of gel materials in controlling viscosity.

The compliant fluid charged material may include pockets of a compressible fluid held within the porous matrix.

It is thus another object of one embodiment of the invention to allow flexible tailoring of the elasticity of the liner independently from its viscous flow properties.

The liquid may be an oil of predetermined viscosity.

It is thus an object of one embodiment of the invention to provide an alternative method of tailoring the viscous properties of the material through the use of different weights of oil.

These particular features and advantages may apply to only some embodiments falling within the claims and thus do not define the scope of the invention.

DETAILED DESCRIPTION OF THE PREFERRED EMBODIMENT

Figure 1:
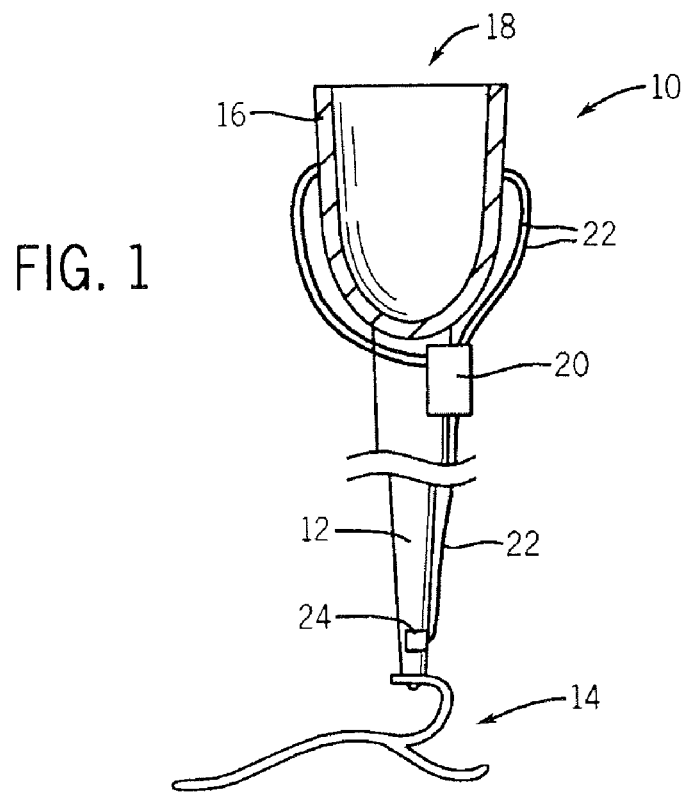
FIG. 1 is a side elevational view in partial cross-section of a prosthetic leg suitable for use with the present invention having an upwardly open socket for receiving the residual limb of the patient and an attached control computer.

Referring now to FIG. 1, a prosthetic leg 10 may include a leg shaft 12 terminating at its lower end with a foot portion 14 and at its upper end by a socket 16. The socket 16 defines a volume 18 opening upwardly to receive the residual limb 28 of a patient (not shown in FIG. 1). A battery powered micro computer 20 may be attached to the prosthetic leg 10 to receive signals over signal lines 22 from valves and sensors in the socket 16 (to be described below) and a stride sensor 24, such as a spring-loaded switch, accelerometer, or strain gauge, sensing force or acceleration on the leg shaft 12 indicating a stride portion of the patient's gait.

Figure 2:
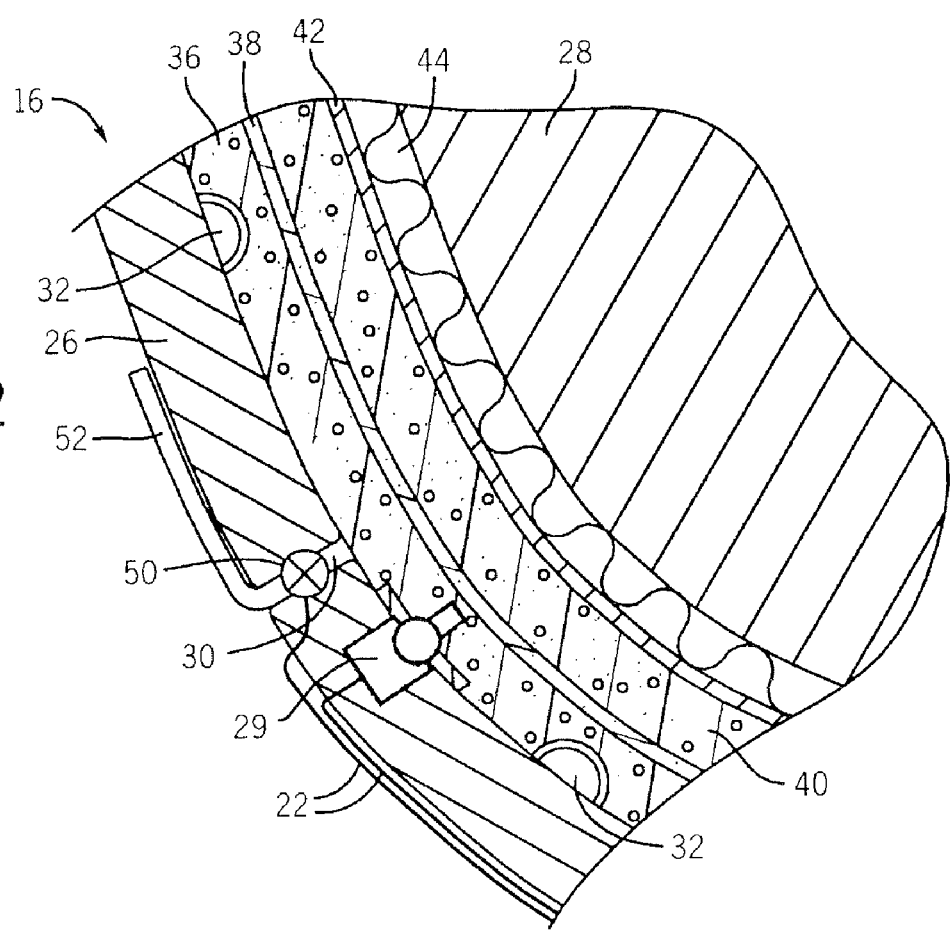
FIG. 2 is a fragmentary cross-section of a portion of the socket of FIG. 1 showing the interface between the residual limb and a set of porous cushioning materials having valves and pressure sensors positioned for local peak pressure control.

Referring now also to FIG. 2, the socket 16 may include an outer rigid shell 26 conforming generally to the outer surface the residual limb 28. The shell 26 may be attached directly to the shaft 12 to communicate forces there between.

At various locations on the inner surface of the shell 26, pressure sensors 29 are placed, near corresponding ports 30 in the shell 26 to be described. The pressure sensors 29 may preferably provided not only normal pressures but also shear pressures and may optionally provide rotational pressures directly or by aggregating shear pressures of multiple adjacent pressure sensors 29. Multi-axis pressure sensors of this type are known in the field of tactile sensing and may use technologies, for example, described in U.S. Pat. Nos. 4,521,685 and 4,745,812. The locations of the pressure sensors 29 will be in areas that are most prone to high contact pressures, for example the medial and lateral tibial supracondyles, medial and lateral tibia, medial and lateral gastrocnemius, patellar tendon, popliteal depression, distal tibia and fibula head.

Also attached to the inner surface of the shell 26 may be air bladders 32 such as will be used to tune the springiness at the interface between the residual limb 28 and the shell 26.

The pressure sensors 29, ports 30, and air bladders 32 are covered with a first permeable foam layer 36 allowing resistive flow of a saturating fluid such as water or oil. A permeable interface layer 38 (or a different permeable foam layer) covers the foam layer 36 separating it from a second permeable foam layer 40 having similar or different resistive flow properties to that of layer 36. The interface layer 38 controls a flow of fluid between the layers 36 and 40 to provide for a general long-term pressure equalization among these layers 36 and 40 moderated by their intrinsic resistance to flow. A flexible impermeable membrane 42 covers layer 40 separating it from the residual limb 28 which may in turn be covered with a sock 44.

The precise viscoelastic properties of the liner formed by layers 36, 38, and 40 may be tailored by changing the viscosity of a fluid within the layers 36 and 40 or the porosity of the matrix through which the fluid flows and the number of air bladders 32. The matrix may be a porous medium such as an elastomeric foam or may be a gel material. The fluid may simply be an oil of known viscosity providing an essentially incompressible fluid.

The ports 30 may each communicate with an electrically actuated valve 50 that may connect the port 30 to a sealed reservoir 52 when the valve 50 is actuated, or disconnect the port 30 from the sealed reservoir 52 when the valve 50 is deactivated. Signal lines 22 from the pressure sensors 29 and a valve 50 may pass through guides on the outer surface of the shell 26 to the computer 20 (not shown).

Figure 3:
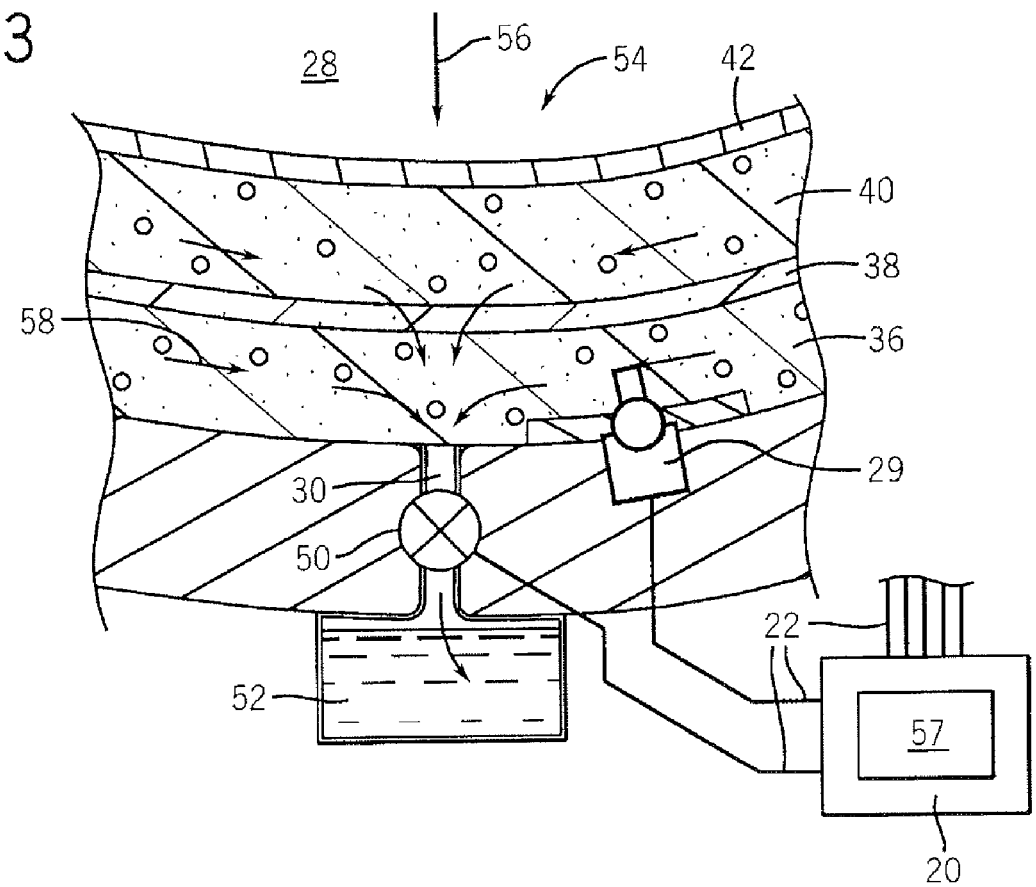
FIG. 3 is a simplified version of FIG. 2 showing fluid flow through the cushioning materials with pressure against the socket by the residual limb in an area where peak pressure is being moderated.
Figure 4:
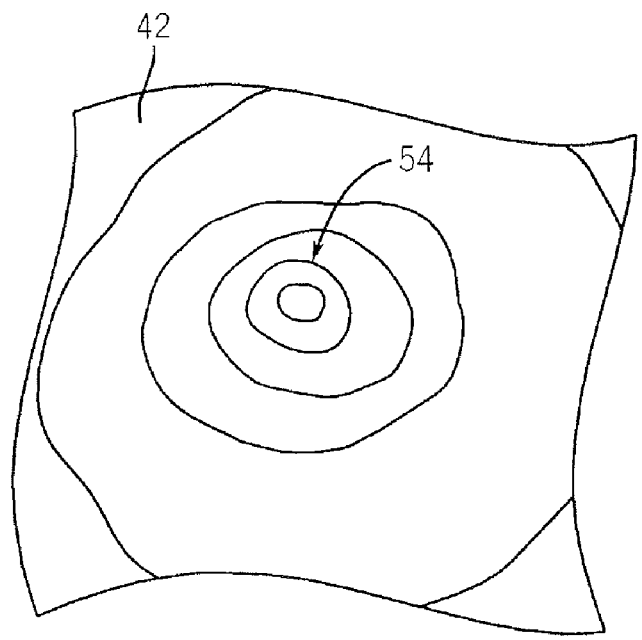
FIG. 4 is a pressure diagram of a region around the valves of FIG. 2 and FIG. 3 showing local boundaries of pressure control possible with the present invention.

Referring now to FIGS. 3 and 4, a local area of low pressure 54 may be dynamically generated about any of the ports 30 by opening the valve 50 so that with pressure 56 by the residual limb 28 against the membrane 42, fluid 58 flows into the port 30 through the valve 50 and into the reservoir 52. Migration of the fluid through the layer 38 and through the layers 36 and 40 controls the size and duration of the low pressure area 54, with higher flow resistance materials localizing the low pressure area and preserving it longer, and lower flow resistance materials expanding the low pressure area 54 but decreasing its duration. The character of the low-pressure area may also be controlled by the size of the port 30, the size of the reservoir 52, and the control of the valve 50 as will be described.

Absent movement of the residual limb 28, the low-pressure area 54 gradually decays and equalizes as liquid flows through these layers 36, 38, and 40.

Figure 5:
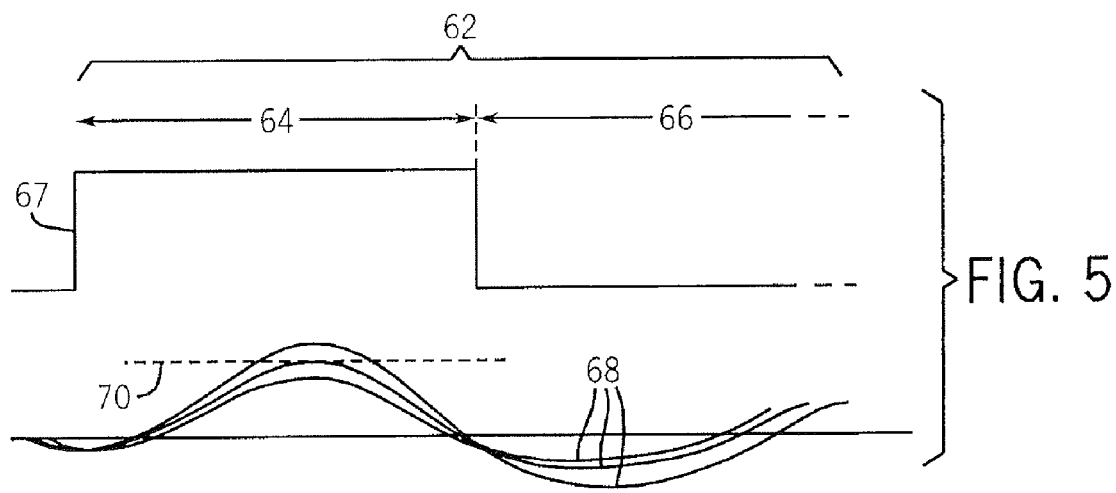
FIG. 5 is a set of graphs showing the use of an external stride cycle signal and a set of corresponding pressure sensing signals used to provide the predictive control system of the present invention.
Figure 6:
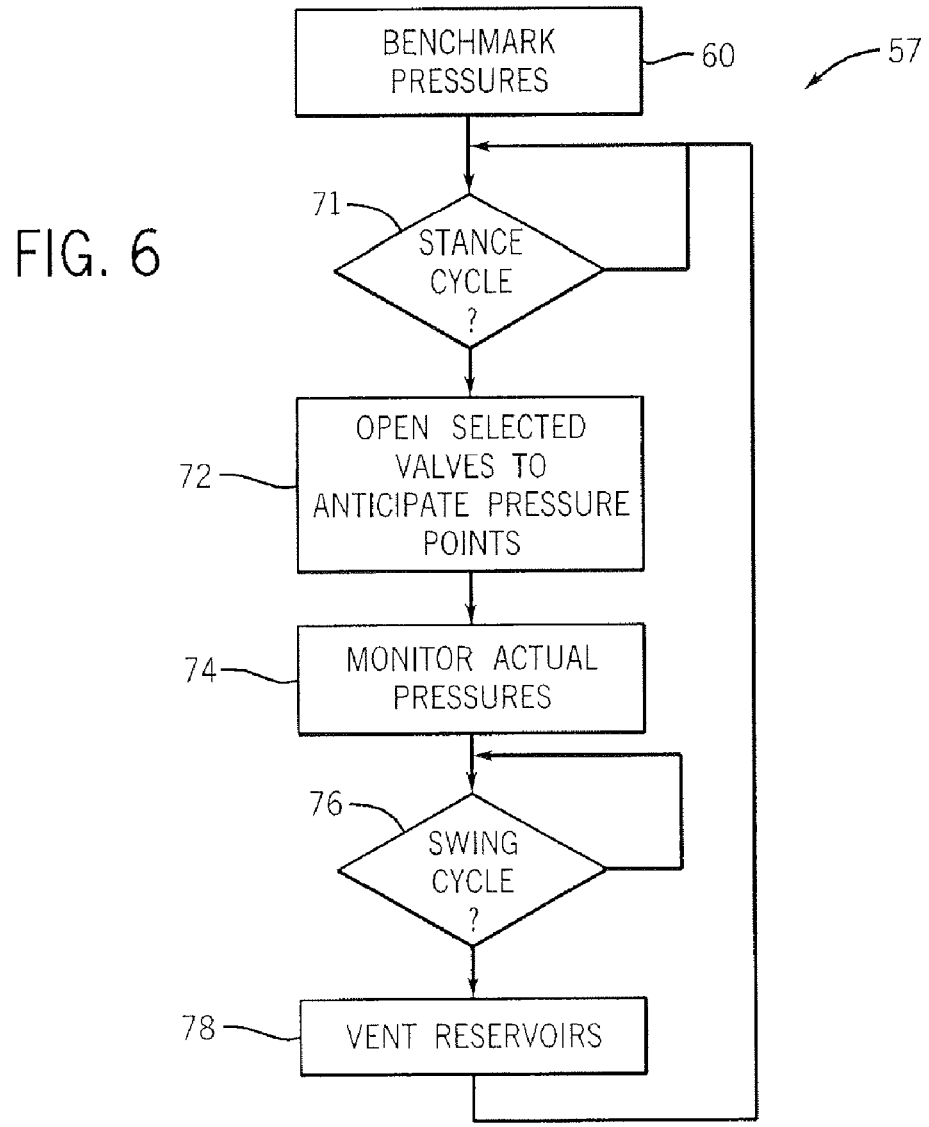
FIG. 6 is a flow chart showing the steps of the program executed on the computer of FIGS. 1 and 3 in effecting the control of the present invention.

Referring now to FIGS. 3, 5, and 6, computer 20 executing a stored program 57 and communicating with the pressure sensors 29 and valves 50 may generate these local, low pressure areas 54, dynamically, and on an anticipatory basis. At process block 60 of the program 57, the program reads a stride signal 67 from the stride sensor 24 during a walking by the patient to benchmark pressure readings from each of the pressure sensors 29. This benchmarking measures pressures at each pressure sensor 29 during a normal stride cycle 62 having a stride portion 64 (when the prosthetic leg 10 is bearing weight) and a swing portion 66 (when the prosthetic leg is not bearing weight).

During the normal stride cycle 62, pressure readings 68 from each of the pressure sensors 29 may be collected and those pressure readings having peak pressures exceeding a predetermined threshold 70 may be identified.

After benchmarking has been obtained per process block 60, the program may proceed to decision block 71 to detect the beginning of the next stride portion 64 (indicated by the rising edge of stride signal 67). At this time as indicated by process block 72, selected valves 50 associated with benchmarked signals from pressure sensors 29 having pressure values exceeding threshold 70 may be opened to anticipate over pressure at the locations of the particular pressure sensors 29. This creates graduated low-pressure areas 54 at those points while maintaining higher pressures outside of these points, the net effect being to counteract the high pressure that would otherwise occur.

The actual pressures reached during the stride portion 64 are then monitored as indicated by process block 74 and then these pressures may be used to create new benchmarks which may be used in the next stride portion 64. In this way, each stride portion 64 takes the data obtained from the previous stride portion 64 and uses that to anticipate conditions during the next stride portion 64. If the pressure associated with the valves 50 opening during the stride portion 64 drops below a predetermined value, the valves 50 may no longer be opened or may be opened for a lesser period of time or less time may be allowed to vent the reservoirs 52 as will be described.

Generally, the process attempts to maintain a high-pressure contact between the socket 16 and the residual limb 28 within the bounds of limit 70.

At process block 76 when a swing cycle is detected as indicated by signal 67 the selected valves 50 that were opened at process block 72 may be reopened to allow the reservoir 52 to vent back into the layers 36, 38 and 40 in preparation for the next stride portion 64 at process block 78.

Generally, the duration of the opening of the valves 50 may be determined according to models developed for the particular materials of the layers 36, 38, and 40 to precisely control a pressure profile over the interface between the residual limb 28 and the socket 16.

The present invention provides localized pressure control independent of the general or average pressure asserted against the residual limb 28 and thus can be used in conjunction with other systems intended to control that average pressure between the residual limb 28 and the socket 16, for example those that use a pump or the like to increased the pressure of liquid within the layers 40 and 36 to accommodate volume changes in the residual limb 28 such as are taught in the prior art.

Different limits 70 may be applied to different regions of the socket 16 and may be manually adjusted by the patient.

It is specifically intended that the present invention not be limited to the embodiments and illustrations contained herein, but include modified forms of those embodiments including portions of the embodiments and combinations of elements of different embodiments as come within the scope of the following claims.

What I claim is:

1. A socket for the attachment of a prosthesis to a residual limb comprising:
    a compliant fluid charged material providing an interface between a rigid shell attached to the prosthesis and the residual limb wherein the compliant fluid charged material comprises a substantially incompressible fluid with a predetermined viscosity moving through at least one porous matrix to provide viscous flow of the fluid under pressure and wherein the compliant fluid charged material further includes pockets of a compressible fluid held within the porous matrix;
    a plurality of pressure sensors, each sensor providing a signal corresponding to the local pressure in the compliant fluid charged material;
    a set of electrically actuated valves providing local control of the pressure between the compliant material and the residual limb;
    a stride sensor connected to the prosthesis and providing a signal indicating a swing cycle of the prosthesis; and
    a micro computer communicating with the stride sensor, the plurality of pressure sensors, and the electrically actuated valves, wherein the micro computer collects the signals from the stride sensor and the plurality of pressure sensors and controls the electrically actuated valves in response to the signals from the stride sensor and the plurality of pressure sensors to adjust the local pressure in anticipation of points of high pressure between the residual limb and the compliant material during the swing cycle.

2. The socket of claim 1 wherein the compliant fluid charged material consists of at least two layers allowing fluid flow therebetween.

3. The socket of claim 1 wherein the porous matrix is an elastomeric foam.

4. The socket of claim 1 wherein the porous matrix is a gel material.

5. The socket of claim 1 wherein the fluid is an oil of predetermined viscosity.

6. A method of controlling a socket for attachment of a prosthesis to a residual limb comprising the steps of:
    (a) preparing a rigid shell conforming loosely to the residual leg and having a means for attachment to the prosthesis and including a compliant fluid charged liner fitting between the residual leg and the shall wherein the compliant fluid charged material comprises a substantially incompressible fluid with a predetermined viscosity moving through at least one porous matrix to provide viscous flow of the fluid under pressure and wherein the compliant fluid charged material further includes pockets of a compressible fluid held within the porous matrix;
    (b) measuring pressure between the residual leg and the shell at a variety of different zones during a swing cycle of the prosthesis identified by a signal from a stride sensor connected to the prosthesis; and
    (c) based on the pressure measurements of step (b), controlling a set of electrically actuated valves providing local control of the pressure between the compliant fluid charged liner and the residual limb to anticipate points of high pressure between the residual limb and the compliant fluid charged liner to adjust local pressures to reduce points of high pressure during the swing cycle of the prosthesis.

7. The method of claim 6 wherein the compliant fluid charged material consists of a least two layers allowing fluid flow therebetween.

8. The method of claim 6 wherein the porous matrix is an elastomeric foam.

9. The method of claim 6 wherein the porous matrix is a gel material.

10. The method of claim 6 wherein the fluid is an oil of predetermined viscosity.

* * * * *